US008821459B2

(12) United States Patent
Stanton et al.

(10) Patent No.: US 8,821,459 B2
(45) Date of Patent: Sep. 2, 2014

(54) REMOVABLE SUCTION ASSEMBLY FOR MEDICAL HANDPIECES

(75) Inventors: Kevin J. Stanton, Naples, FL (US); James Hamer, Naples, FL (US); Philip S. O'Quinn, Naples, FL (US); Kenneth M. Adams, Naples, FL (US); Randall L. Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 659 days.

(21) Appl. No.: 13/093,443

(22) Filed: Apr. 25, 2011

(65) Prior Publication Data

US 2011/0202023 A1    Aug. 18, 2011

Related U.S. Application Data

(63) Continuation-in-part of application No. 12/783,417, filed on May 19, 2010, which is a continuation-in-part of application No. 12/561,866, filed on Sep. 17, 2009.

(51) Int. Cl.
*A61M 1/00* (2006.01)

(52) U.S. Cl.
CPC .................................. *A61M 1/0043* (2013.01)
USPC .......................................... 604/319; 604/535

(58) Field of Classification Search
CPC ............ A61M 1/0023; A61M 1/0039; A61M 1/0041; A61M 1/0043; A61M 1/008; A61M 1/0084; A61M 39/1055
USPC .......................... 604/22, 27, 30, 35, 540, 542
See application file for complete search history.

(56) References Cited

U.S. PATENT DOCUMENTS

| 5,957,945 A * | 9/1999 | Bays ............................ 606/180 |
| 2004/0158203 A1 | 8/2004 | Cover et al. |
| 2008/0145816 A1 | 6/2008 | Hershey et al. |
| 2011/0065997 A1 | 3/2011 | Hamer et al. |
| 2011/0066122 A1 | 3/2011 | Stanton et al. |

* cited by examiner

*Primary Examiner* — Melanie Hand
(74) *Attorney, Agent, or Firm* — Dickstein Shapiro LLP

(57) ABSTRACT

A system and method for more efficient cleaning and sterilizing of surgical handpieces by using a removable valve assembly. The valve assembly is removable to provide access to a first suction passageway and a second suction passageway for cleaning purposes. The valve assembly has a protrusion that engages with a handpiece to secure the assembly to the handpiece. The protrusion of the valve assembly may also be retracted into the valve assembly to allow the valve assembly to disengage the handpiece thereby allowing the valve assembly to be removed from the handpiece. The first suction passageway may also be removable.

21 Claims, 17 Drawing Sheets

REMOVABLE SUCTION ASSEMBLY FOR MEDICAL HANDPIECES

CROSS-REFERENCE TO RELATED APPLICATIONS

This application is a continuation-in-part of application Ser. No. 12/783,417, filed on May 5, 2010, which is a continuation-in-part of application Ser. No. 12/561,866, filed on Sep. 17, 2009, the entire disclosures of which are incorporated by reference herein.

FIELD OF THE INVENTION

The present invention relates to systems and methods related to medical handpieces having suction passageways, and to rotating or other moving elements driven by a motor within the handpiece.

DESCRIPTION OF THE RELATED ART

Powered handpieces are commonly used in many medical specialties to drive surgical blades for performing various diverse cutting functions including resection, comminution, dissection, debridement, shaving, drilling, pulverizing and shaping of anatomical tissue. In arthroscopic surgery, powered or motorized handpieces and systems have been proposed as illustrated by the ADAPTEUR™ POWER (APSII) system of Arthrex, Inc. Naples, Fla.; Stryker CORE SHAVER SYSTEM of Stryker Endoscopy; and the ADVANTAGE System of Linvatec, Incorporated, Largo, Fla.

Conventional powered handpieces are typically all metal and reusable in design with permanently installed motors. Conventional powered handpieces generally use suction to evacuate anatomical tissue cut or excised by the blades or burrs. Powered handpieces currently in use generally force the excised anatomical tissue to follow a suction path which passes through the handpiece itself Such handpieces are typically decontaminated and sterilized for reuse by steam autoclave and/or soaking in a disinfectant solution. The dissected tissue travels through portions of the suction passageways which reside within the handpiece. As a result, it is sometimes difficult to access the entire suction passageway during the cleaning and sterilization process to effectively remove tissue debris from within the suction passageways of the handpiece. Tissue debris left within the handpiece may result in contamination during the next surgical use of the handpiece.

BRIEF SUMMARY OF THE INVENTION

The present invention provides systems and methods for more efficient cleaning and sterilizing surgical handpieces by using a removable valve assembly. The valve assembly is removably attached to a surgical handpiece and connects a first suction passageway to a second suction passageway. The valve assembly is removable to provide access to the first and second suction passageways for cleaning purposes. At least one of the first or second suction passageways may also be removable.

In accordance with the present invention, a surgical handpiece is provided which includes a first suction passageway, a second suction passageway and a removable valve assembly which connects the first suction passageway to the second suction passageway when the valve is in an open position. The valve assembly includes a protrusion. The protrusion engages the handpiece to secure the valve assembly to the handpiece. The protrusion disengages the valve assembly from the handpiece by retracting away from the handpiece, and a portion of the protrusion enters the valve assembly when the protrusion retracts away from the handpiece. A spring can be used to cause the protrusion to engage with the handpiece. The part of the protrusion that engages with the handpiece may have a spherical shape.

BRIEF DESCRIPTION OF THE DRAWINGS

The foregoing aspects and other aspects of this disclosure are described in detail below in connection with the accompanying drawing figures in which.

DETAILED DESCRIPTION OF THE PREFERRED EMBODIMENTS

The present invention provides systems and methods for more efficient cleaning and sterilizing of surgical handpieces by using a removable valve assembly. The valve assembly is removably attached to a surgical handpiece and connects a first suction passageway to a second suction passageway. The valve assembly is removable to provide access to the first and second suction passageways for cleaning purposes. At least one of the first or second suction passageways may also be removable.

The present invention also provides methods for efficient cleaning and sterilizing of surgical handpieces by using a removable valve assembly. According to an exemplary embodiment only, the method of the present invention comprises the steps of: (i) providing a surgical handpiece with a removable valve assembly connecting a first suction/aspiration passageway and a second suction/aspiration passageway in the proximity of a surgical site; (ii) conducting at least one surgical procedure involving removal of anatomical tissue from the surgical site; (iii) removing the valve assembly; and (iv) cleaning a portion of the first and second suction/aspiration passageways that were previously inaccessible, to remove tissue debris from the at least one of the first and second suction/aspiration passageways.

Figure 1:
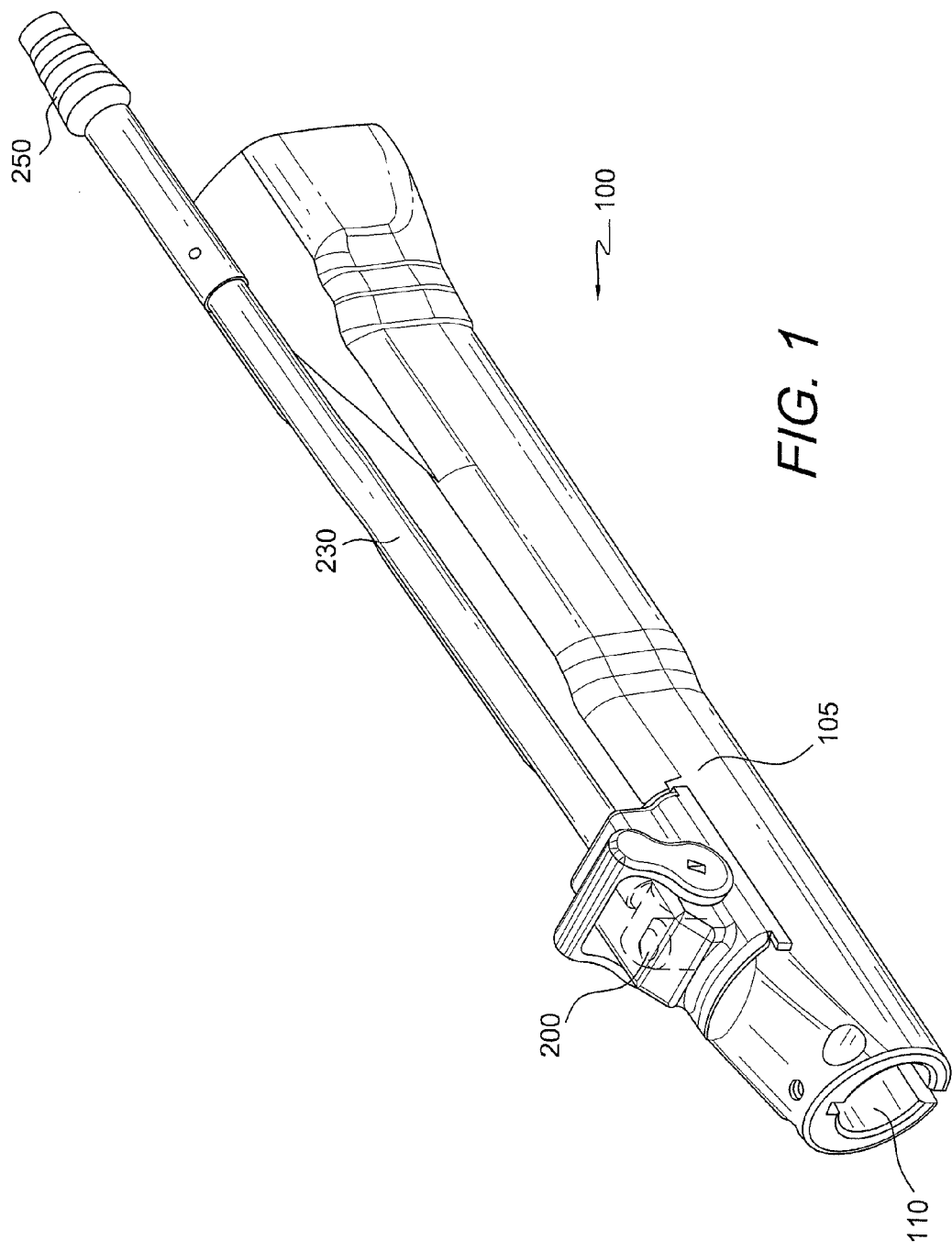
FIG. 1 is a perspective view of a powered handpiece according to an exemplary embodiment of the present invention.

Referring now to the drawings, where like elements are designated by like reference numerals, FIGS. 1-12 illustrate various structural elements of handpiece 100 of the present invention provided with valve assembly 200 and operatively connected to a surgical instrument 300. In an exemplary embodiment, and as shown in FIG. 1, handpiece 100 is a motorized, reusable surgical handpiece 100 (FIG. 1) configured to operate a variety of disposable (or reusable) surgical instruments. The handpiece 100 has a generally cylindrical shape and includes a housing 105. At its distal end, the handpiece 100 includes a cylindrical bore 110 for attachment of a surgical instrument. Located within the housing 105, a drive shaft 115 is coupled to a motor 120 also positioned within the handpiece 100. The handpiece may include a controlling means such as pushbuttons 125 and 135 or a foot control assembly, for example, that produces signals for use in controlling the motor.

The handpiece 100 is fully autoclavable. The handpiece 100 is preferably made of durable, medically acceptable materials, such as metal or plastic, including stainless steel, hard coat anodized aluminum, titanium, Ultem, PEEK, or Radel, capable of being sterilized to medical standards, such as by steam or flash autoclaving, gas sterilization and/or soaking in a disinfectant solution.

The handpiece 100 is employed in a surgical system that includes the handpiece, a console, a surgical instrument 300 (FIG. 2) or a set of surgical instruments, and optionally a foot control assembly. A processor positioned within the console controls the operating speed and direction of the motor of the handpiece 100. This, in turn, controls the operating speed and direction of the surgical instrument 300. For example, when the surgical instrument 300 includes an active portion 305 (such as a cutting blade or an abrading burr) that rotates about the longitudinal axis of the handpiece 100, the processor controls the direction and speed at which the active portion 305 rotates.

The processor controls the motor 120 in response to signals from the pushbuttons 125 and 135, the console, and/or the foot control assembly. The handpiece 100 is connected to the console by a cable that is attached to the proximal end of the handpiece.

Figure 2:
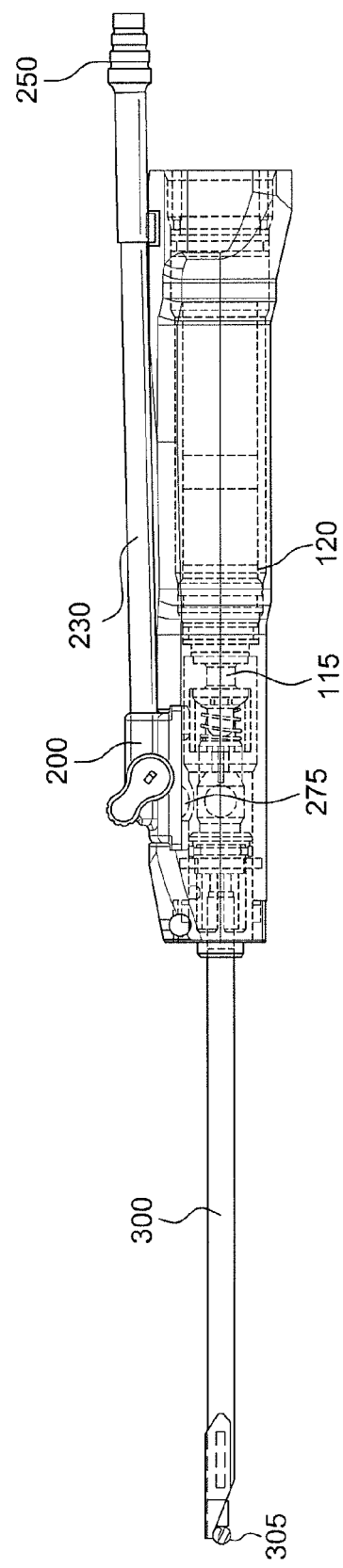
FIG. 2 is a side view of the powered handpiece of FIG. 1 (and with a surgical instrument attached to the powered handpiece)

A surgical instrument such as a shaver includes a drive shaft having an opening that permits material drawn through the inner tube of the surgical instrument to pass into the suction/aspiration passageway 230 of the handpiece 100. The suction/aspiration passageway 230 ends at barb connection 250 at the proximal end of the handpiece. During use, the barb connection 250 is connected to a source of suction (not shown). The handpiece 100 also includes a valve assembly 200 that controls flow through the suction/aspiration passageway 230. As shown in FIGS. 1 and 2, the valve assembly 200 is positioned on the handpiece near the distal end. In the open position, the valve assembly 200 allows fluid and material such as tissue debris to flow from the surgical instrument 300 through suction/aspiration passageway 275 created within bore 110 when the surgical instrument 300 is in place and the suction/aspiration passageway 230 of the handpiece 100. In the closed position, the valve assembly 200 stops the flow through the suction/aspiration passageway 230 and suction/aspiration passageway 275 from the surgical instrument through the handpiece.

At the end of a surgical procedure, the surgical instrument 300 (FIG. 2) is removed from the handpiece 100. The handpiece 100 is cleaned and sterilized for reuse. Tissue debris may be trapped along portions of the suction/aspiration passageways 275, 230. Accessing the entire suction/aspiration passageway to remove all tissue debris can be difficult. In the current invention, and as detailed in FIG. 3, for example, the valve assembly 200 is removable from the handpiece 100 and may also be disposable. By making the valve assembly 200 removable, it is possible to remove the portion of the suction/aspiration passageway that tends to accumulate the most tissue debris for thorough cleaning or disposal and replacement with a clean valve assembly. It also provides access to the inner, more remote portions of the suction/aspiration passageway that previously were either difficult to access or inaccessible. Removing the valve assembly 200 allows for direct access to suction/aspiration passageway 230 and opening 270 within the handpiece leading to bore 110 and suction/aspiration passageway 275. A brush, other cleaning instrument, or flushing instrument can be used through opening 270 to clean the suction/aspiration passageway 275 within bore 110 or through suction/aspiration passageway 230 and remove any remaining debris.

Figure 9:
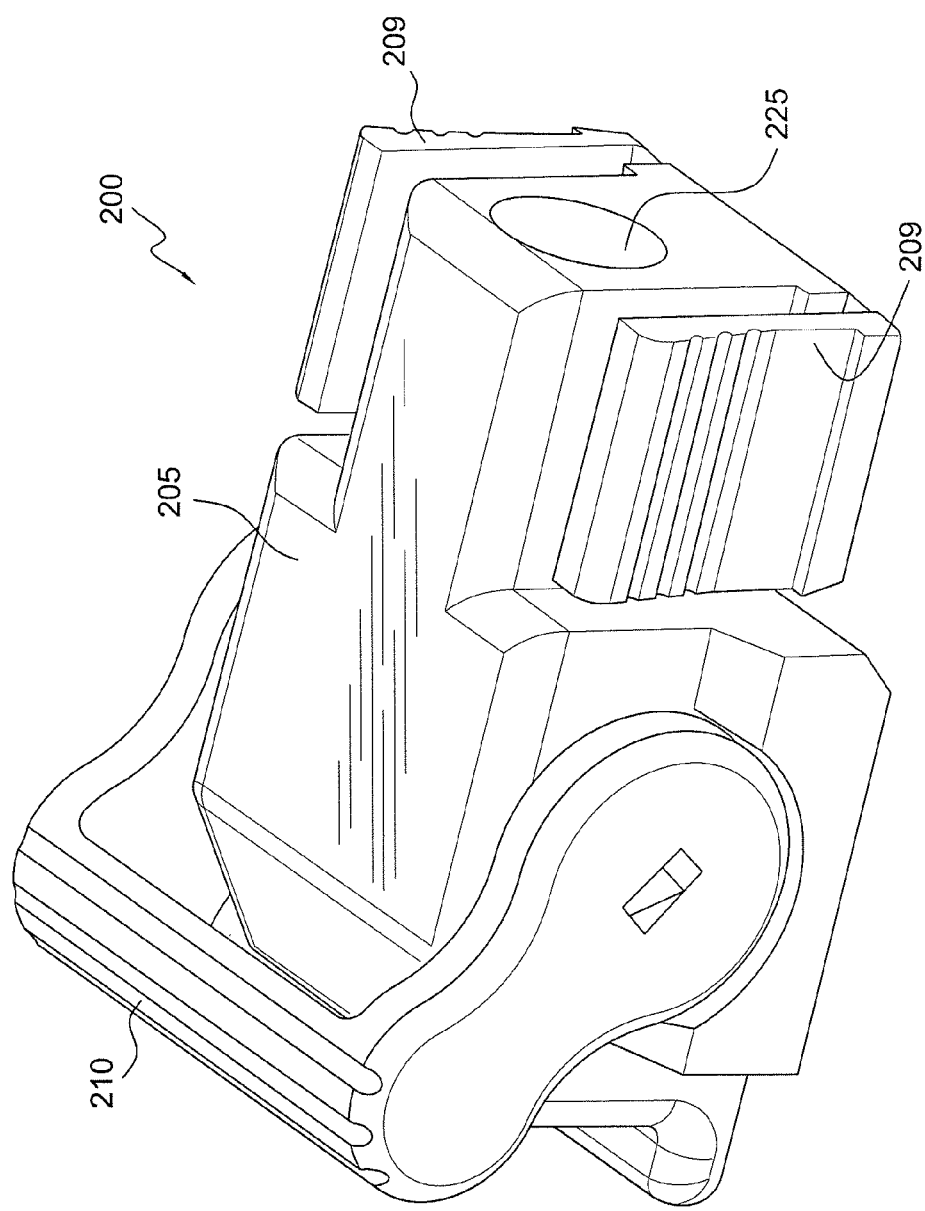
FIG. 9 illustrates an enlarged, perspective view of an embodiment of the removable suction valve assembly according to the present invention.
Figure 10:
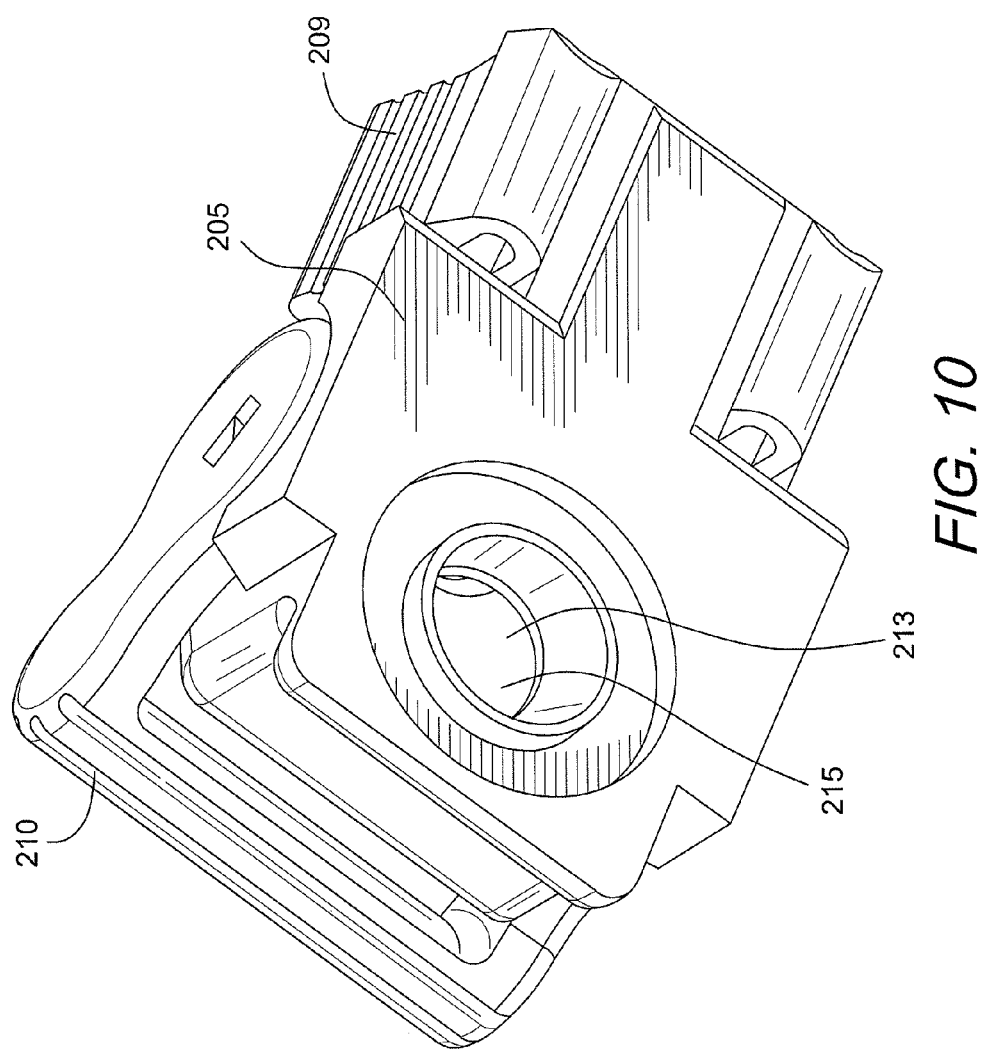
FIG. 10 illustrates a bottom view of the removable suction valve assembly of FIG. 9.

Details of the valve assembly 200 are illustrated in FIGS. 9 and 10. Body 205 of the valve assembly 200 has a lever 210 for opening and closing the barrel/valve 215 to allow or prevent flow through the suction/aspiration passageway 230 of the handpiece 100. Body 205 has an opening 213 (FIG. 10) for communicating with the suction/aspiration passageway 275 within bore 110 leading from the surgical instrument. Body 205 also has an opening 225 (FIG. 9) communicating with the suction/aspiration passageway 230 leading from the handpiece. Body 205 is removable from the handpiece 100 allowing access to portions of the suction/aspiration passageway. In an exemplary embodiment shown in FIGS. 1 and 3, valve assembly 200 may slidingly engage the handpiece in a unidirectional manner having stops 207 to prevent the valve assembly from sliding completely out of the handpiece. In an alternate embodiment, shown in FIGS. 9 and 10, the valve assembly may be removable from the handpiece using a snap-fit connection with push-in tabs 209. The valve assembly may be removable in any number of ways known to one skilled in the art including a twist-in fashion. The valve assembly may be made from plastic or metal materials, such as stainless steel, aluminum or injection moldable materials like polycarbonate, ultem, PEEK, Radel or ABS.

Figure 13:
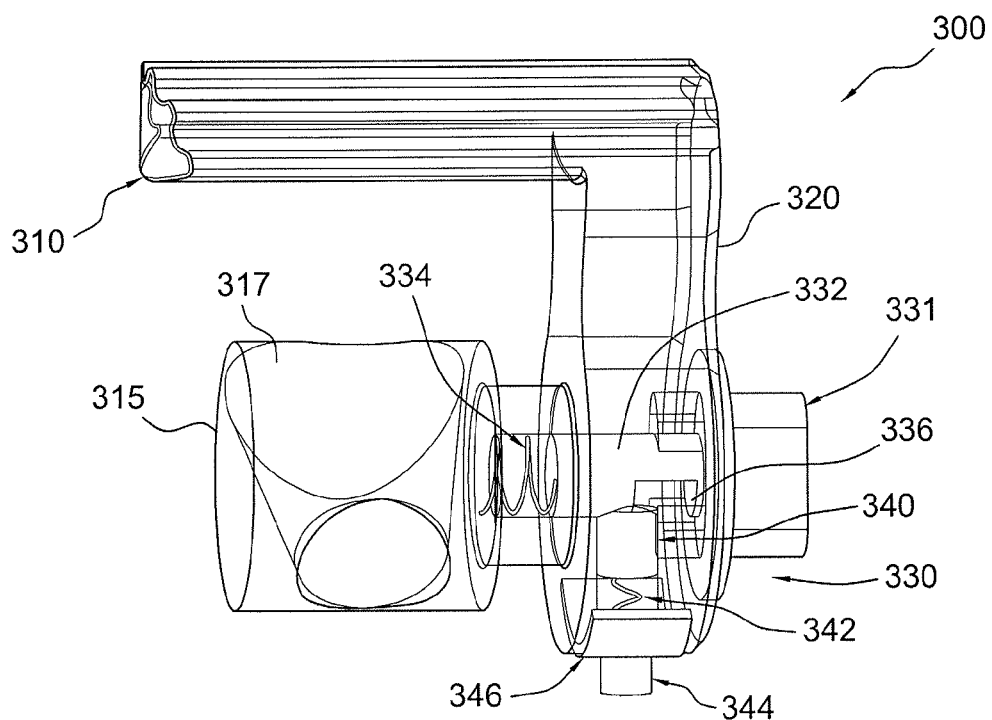
FIG. 13 illustrates another embodiment of the removable suction valve assembly.

Another embodiment of valve assembly 300 is illustrated in FIG. 13. In this embodiment, valve assembly 300 includes handle 310, valve 315, and body 320. The valve assembly 300 further includes securing system 330 that includes pin knob 331, pin shaft 332, pin spring 334, pin notch 336, protrusion pin 340, protrusion spring 342, protrusion 344, and protrusion plate 346.

Valve 315 has a cylindrical shape and a circular opening 317 that extends through valve 315. Valve 315 is attached to body 320, which is attached to handle 310. As a result, when handle 310 is moved it rotates valve 315. When valve assembly 300 is attached to handpiece 800 (FIG. 18), valve 315 may be rotated so that opening 317 is aligned with suction passageways of handpiece 800, thereby connecting and allowing matter to pass from one suction passageway to another. Valve 315 may also be rotated so that opening 317 is not aligned with suction passageways of handpiece 800, thereby disconnecting the suction passageways from each other.

Valve assembly 300 may be placed within a cavity in handpiece 800. To secure valve assembly 300 within the cavity, protrusion 344 engages with handpiece 800. Protrusion 344 may be extended and retracted to allow protrusion 344 to engage and disengage handpiece 800. This allows valve assembly 300 to be secured to handpiece 800 and to be subsequently removed from the cavity of handpiece 800. Protrusion 344 engages and disengages handpiece 800 using securing system 330.

Securing system 330 includes pin knob 331 that is coupled to pin shaft 332 and pin spring 334. Pin spring 334 pushes pin shaft 332 and pin knob 331 away from the valve 315 and keeps pin notch 336 from the center of body 320. A force may be applied to pin knob 331, depressing pin knob 331 toward body 320. This causes pin shaft 332 to shift, thereby shifting pin notch 336 into the center of body 320 and compressing pin spring 334. When pin notch 336 is in the center of body 320, it aligns with protrusion pin 340. Protrusion spring 342 causes protrusion pin 340 to shift into pin notch 336. As protrusion pin 340 shifts into pin notch 336, protrusion 344 retracts into body 320. Protrusion plate 346 functions to retain protrusion 344, protrusion spring 342, and protrusion pin 340 within body 320.

With protrusion 344 retracted, valve assembly 300 disengages handpiece 800 so that valve assembly 300 may be removed from the cavity of handpiece 800. If force is no longer applied to pin knob 331, pin spring 334 shifts pin notch 336 away from the center of body 320. This causes protrusion pin 340 to shift and compress protrusion spring 342. As protrusion spring 342 compresses, it extends protrusion 344 away from body 320. To reinstall valve assembly 300 into the cavity of handpiece 800, pin knob 331 is depressed, causing protrusion 344 to retract within body 320 and allowing valve assembly 300 to be installed.

Figure 14:
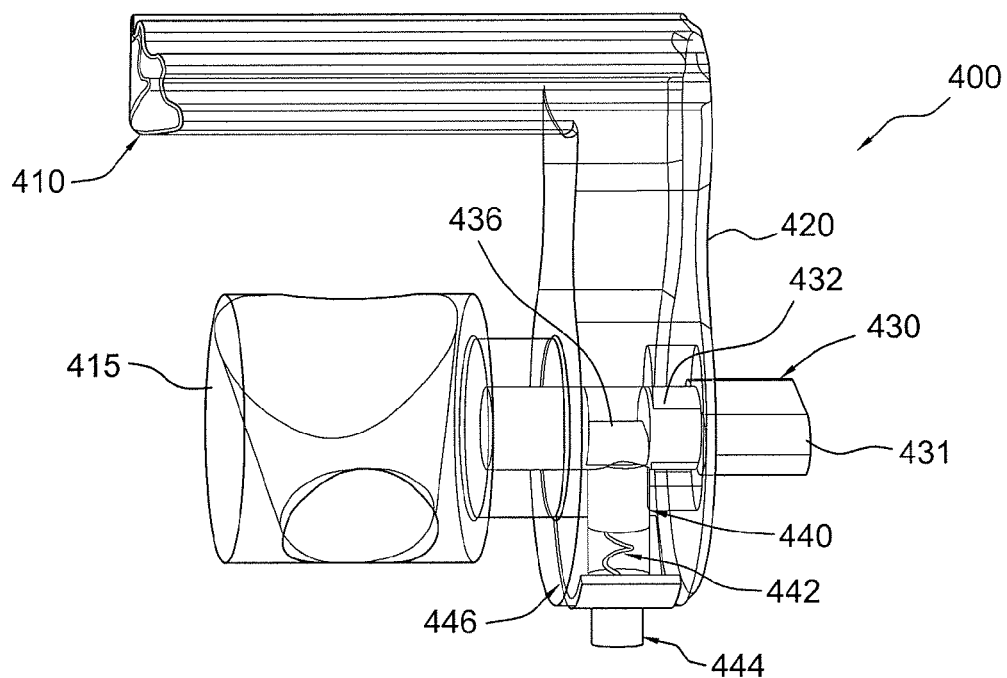
FIG. 14 illustrates another embodiment of the removable suction valve assembly.

Another embodiment of valve assembly 400 is illustrated in FIG. 14. In this embodiment, valve assembly 400 includes handle 410, valve 415, and body 420. The valve assembly 400 further includes securing system 430 that includes pin knob 431, pin shaft 432, pin notch 436, protrusion pin 440, protrusion spring 442, protrusion 444, and protrusion plate 446.

Valve 415 has a cylindrical shape and a circular opening that extends through valve 415 and functions similar to valve 315. Valve assembly 400 may be placed within a cavity in handpiece 800. To secure valve assembly 400 within the cavity, protrusion 444 engages with handpiece 800. Protrusion 444 may be advanced and retracted to allow protrusion 444 to respectively engage and disengage handpiece 800. This allows valve assembly 400 to be secured to handpiece 800 and to be subsequently removed from the cavity of handpiece 800. Protrusion 444 engages and disengages handpiece 800 using securing system 430.

Securing system 430 includes pin knob 431 that is coupled to pin shaft 432 that has pin notch 436. Pin knob 431 may be rotated allowing protrusion pin 440 to shift into pin notch 436. Protrusion spring 442 causes protrusion pin 440 to shift into pin notch 436. As protrusion pin 440 shifts into pin notch 436, it retracts protrusion 444 into body 420. Protrusion plate 446 functions to retain protrusion 444, protrusion spring 442, and protrusion pin 440 within body 420.

With protrusion pin 444 retracted, valve assembly 400 disengages handpiece 800 so that valve assembly 400 may be removed from the cavity of handpiece 800. To reinstall valve assembly 400 into the cavity of handpiece 800, pin knob 431 is turned causing protrusion 444 to retract within body 420 and allowing valve assembly 400 to be installed. Once valve assembly 400 is installed within handpiece 800, pin knob 431 is rotated causing protrusion 444 to extend away from body 420 and engage handpiece 800, thereby securing valve assembly 400 to handpiece 800.

Figure 15:
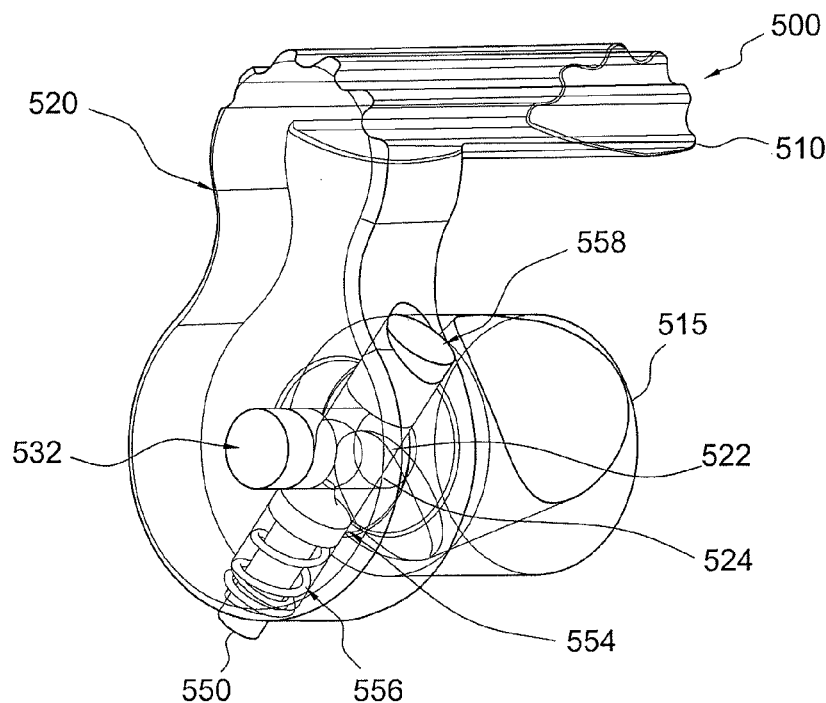
FIG. 15 illustrates another embodiment of the removable suction valve assembly.

Another embodiment of valve assembly 500 is illustrated in FIG. 15. In this embodiment, valve assembly 500 includes handle 510, valve 515, body 520, protrusion shaft 522, and pin shaft 524. Pin shaft 524 intersects protrusion shaft 522 at approximately a right angle. Valve assembly 500 further includes securing system 530 that includes pin 532, retaining pin 558, protrusion spring 556, and protrusion pin 550. Protrusion pin 550 has protrusion pinhead 554 at one end, pinhead 554 having a larger circumference than the remainder of pin 550.

Valve 515 has a cylindrical shape and a circular opening that extends through valve 515 and functions similar to valve 315. Valve assembly 500 may be placed within a cavity in handpiece 800. To secure valve assembly 500 within the cavity, protrusion pin 550 engages with handpiece 800. Protrusion pin 550 may be extended and retracted to allow valve assembly 500 to be secured to handpiece 800 and to be subsequently removed from the cavity of handpiece 800. In contrast to other embodiments, valve assembly 500 may only be used once and there are no parts that may be removed.

Securing system 530 includes protrusion pin 550 and protrusion spring 556 located in protrusion shaft 522. Protrusion shaft 522 has one opening that is large enough to allow protrusion spring 556 and protrusion pin 550 to enter shaft 522. To retain spring 556 and pin 550 within shaft 522, retaining pin 558 is placed in the end of shaft 522. The other opening of shaft 522 is large enough to allow part of protrusion pin 550 to pass but not protrusion spring 556, nor protrusion pinhead 554. In protrusion shaft 522, protrusion pin 550 passes through protrusion spring 556 and protrusion spring 556 engages with protrusion pinhead 554. As a result, protrusion spring 556 keeps protrusion pin 550 within protrusion shaft 522.

To overcome the force of protrusion spring 556 and to shift protrusion pin 550 and cause protrusion pin 550 to extend away from body 530, pin 532 is pushed into pin shaft 524. As pin 532 is pushed into pin shaft 524, pin 532 engages and displaces pinhead 554 and shifts pin head 554 causing protrusion pin 550 to extend away from body 520. As protrusion pin 550 extends away from body 520 it may engage with handpiece 800, thereby securing valve assembly 500 to handpiece 800. To retract protrusion pin 550, pin 532 is further pushed into pin shaft 524. As pin 532 disengages pinhead 554, spring 556 retracts protrusion pin 550 into body 520. As a result, protrusion pin 550 may disengage handpiece 800 and free valve assembly 500 from handpiece 800. However, as a result, pin 532 is located within valve assembly 500 and valve assembly 500 may not be used again.

Figure 16:
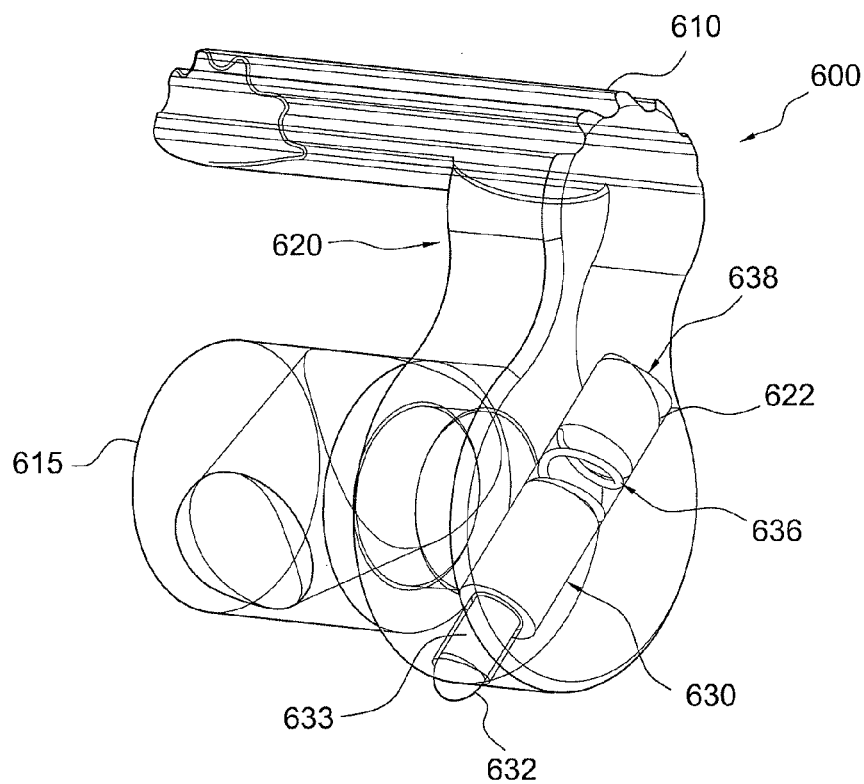
FIG. 16 illustrates another embodiment of the removable suction valve assembly.

Another embodiment of valve assembly 600 is illustrated in FIG. 16. In this embodiment, valve assembly 600 includes handle 610, valve 615, body 620, and shaft 622. Valve assembly 600 further includes securing system 630 that includes protrusion pin 632, protrusion spring 636, and retaining pin 638. Protrusion pin 632 has protrusion pin body 633 and protrusion pinhead 634, pinhead 634 having a larger circumference than pin body 633. Further, an end of pin body 633 may have a spherical shape.

Valve 615 has a cylindrical shape and a circular opening that extends through valve 615 and functions similar to valve 315. Valve assembly 600 may be placed within a cavity in handpiece 800. To secure valve assembly 600 within the cavity, protrusion pin 632 engages with handpiece 800. Protrusion pin 632 may be extended and retracted to allow protrusion 632 to engage and disengage handpiece 800. This allows valve assembly 600 to be secured to handpiece 800 and to be subsequently removed from the cavity of handpiece 800. Protrusion pin 632 engages and disengages handpiece 800 using securing system 630.

Securing system 630 includes protrusion pin 632 and protrusion spring 636 located in protrusion shaft 622. Protrusion shaft 622 has one opening that is large enough to allow protrusion spring 636 and protrusion pin 632 to enter shaft 622. To retain spring 636 and pin 632 within shaft 622, retaining pin 638 is placed in the end of shaft 622. The other opening of shaft 622 is large enough to allow pin body 633 to pass but not pin head 634. In protrusion shaft 622, protrusion spring 636 is placed between protrusion pin 632 and retaining pin 638. Spring 636 applies a constant force to protrusion pinhead 634 causing protrusion pin body 633 to extend out of shaft 622 and away from body 620. Protrusion pin 632 does not completely exit shaft 622 since the opening of shaft 622 through which protrusion pin body 633 extends is too narrow to allow protrusion pinhead 634 to pass. Protrusion pin body 633 may be retracted into body 620 by applying a force to protrusion pin 632 sufficient to compress spring 636.

With protrusion pin body 633 extended it may engage with handpiece 800, thereby securing valve assembly 600 to handpiece 800. To disengage valve assembly 600 from handpiece 800, a force needs to be applied to protrusion pin body 633 to cause pin body 633 to retract into body 620.

Figure 17:
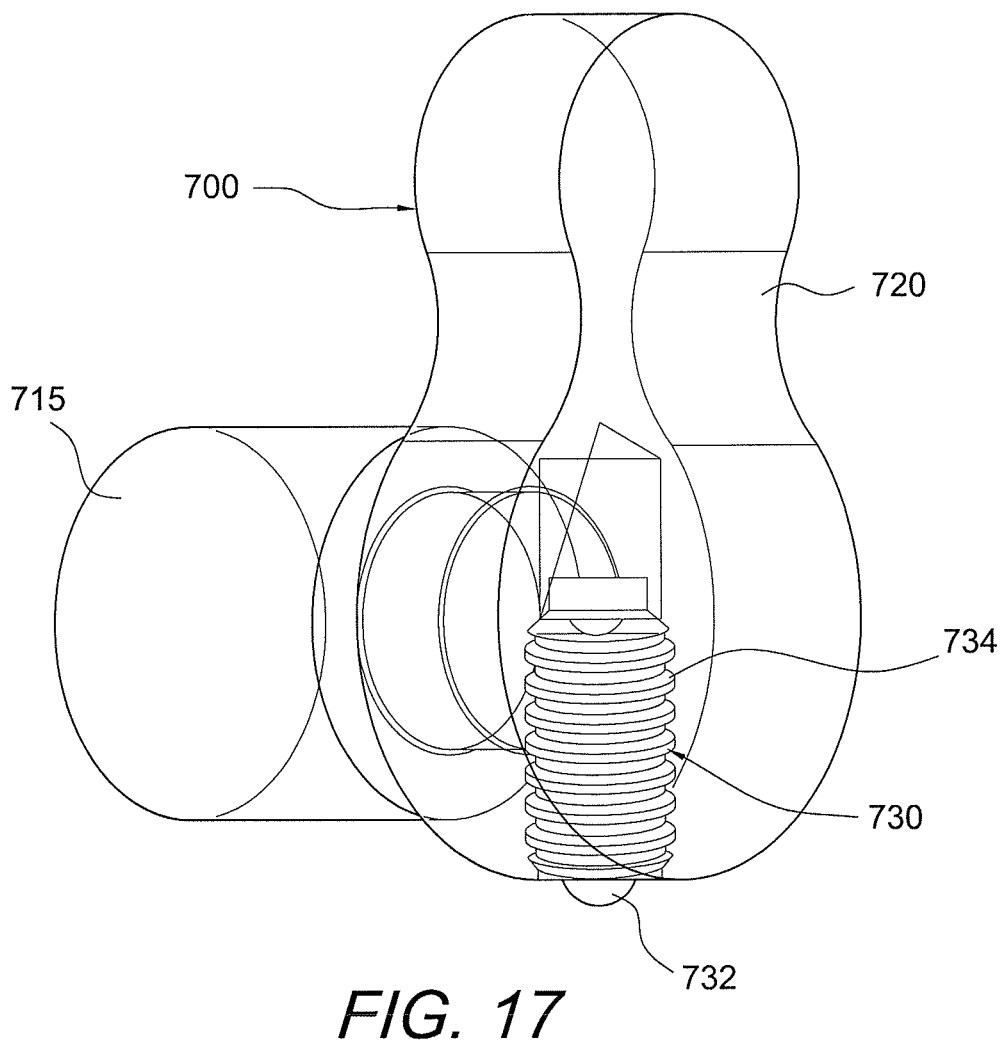
FIG. 17 illustrates another embodiment of the removable suction valve assembly.

Another embodiment of valve assembly 700 is illustrated in FIG. 17. In this embodiment, valve assembly 700 includes valve 715 and body 720. Valve assembly 700 further includes securing system 730 that includes protrusion pin 732 and plunger 734. An end of pin 732 may have a spherical shape.

Valve 715 has a cylindrical shape and a circular opening that extends through valve 715 and functions similar to valve 315. Valve assembly 700 may be placed within a cavity in handpiece 800. To secure valve assembly 700 within the cavity, protrusion pin 732 engages with handpiece 800. Protrusion pin 732 may be extended and retracted to allow protrusion pin 732 to engage and disengage handpiece 800. This allows valve assembly 700 to be secured to handpiece 800 and to be subsequently removed from the cavity of handpiece 800. Protrusion pin 732 engages and disengages handpiece 800 using securing system 730.

Securing system 730 includes protrusion pin 732 and plunger 734 located within body 720. Plunger 734 is a tube with a spring that pushes protrusion pin 732 away from body 720. Pin 732 may be pushed in and out of body 720 in a manner similar to that shown with regard to valve assembly 600.

With protrusion pin 732 extended it may engage with handpiece 800, thereby securing valve assembly 700 to handpiece 800. To disengage valve assembly 700 from handpiece 800, a force needs to be applied to protrusion pin 732 to cause pin 732 to retract into body 720.

Figure 18:
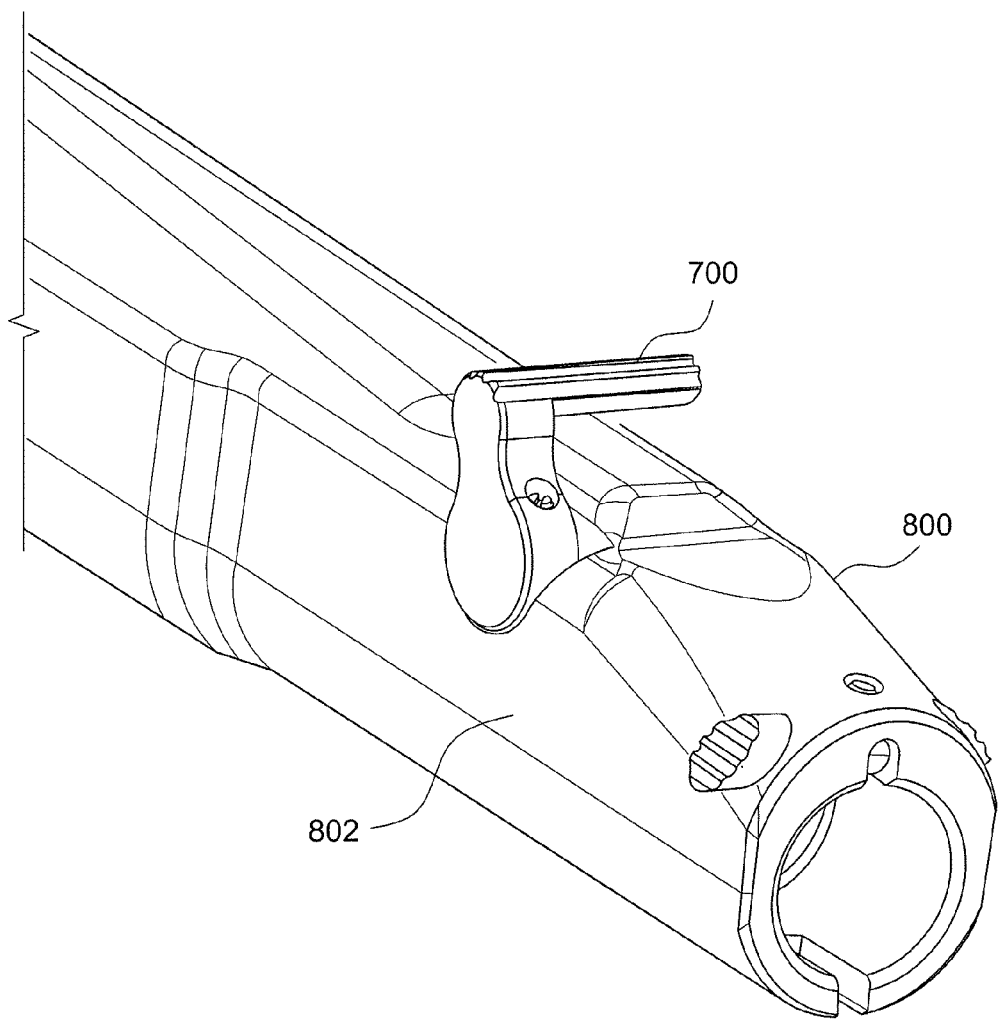
FIG. 18 illustrates a removable suction valve assembly within a handpiece.

FIG. 18 shows valve assembly 700 within a cavity of handpiece 800. Valve assembly 700 may be removed by pushing or pulling valve assembly 700 away from handpiece side 802. The force applied to valve assembly 700 may be approximately normal to the force of the spring in plunger 734 and may be applied by a human hand. As the force is applied it may cause a rounded tip of pin 732 to come into contact with handpiece 800. Handpiece 800 may apply a force on pin 732 to overcome the force of the spring in plunger 734 and pin 732 may retract into body 720. In this manner, pin 732 disengages handpiece 800 so that valve assembly 700 may be removed from handpiece 800.

Figure 19:
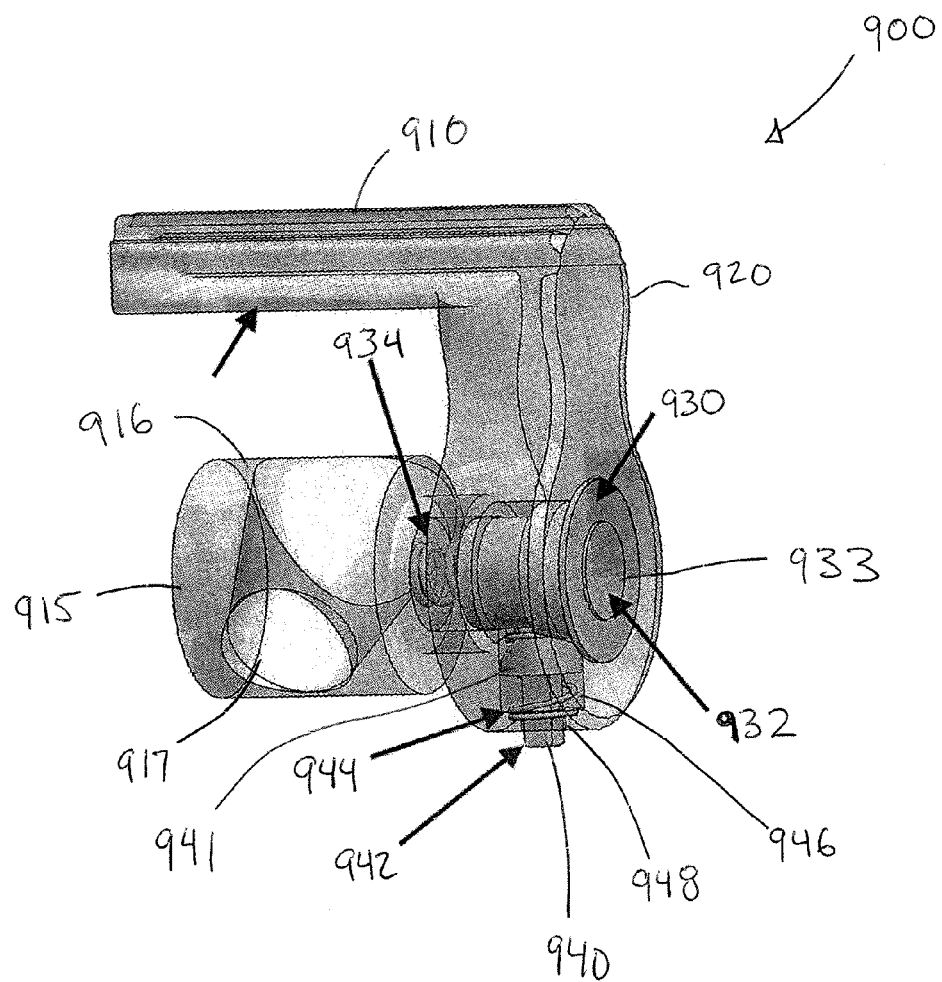
FIG. 19 illustrates another embodiment of the removable suction valve assembly.

Another embodiment of valve assembly 900 is illustrated in FIG. 19. In this embodiment, valve assembly 900 includes handle 910, valve 915, body 920, and securing system 930.

Handle 910, valve 915, and body 920 form a unitary structure with both handle 910 and valve 915 extending away from body 920 in the same direction. Handle 910, valve 915, and body 920 may be integrally formed or handle 910 and valve 915 may be formed separately and then connected to body 920. Valve 915 has a cylindrically shaped body 916 with flat ends and a circular shaft or opening 917 that extends latitudinally through valve body 916 and runs parallel to the flat ends of valve body 916.

Securing system 930 is located in body 920 and includes action pin 932, pin spring 934, protrusion pin 940, and protrusion spring 944. Action pin 932 has a cylindrically shaped shaft with a varying diameter that extends latitudinally at least partially through body 920 in a direction perpendicular to opening 917 and is able to move latitudinally within body 920. Action pin 932 also includes a circular pressing end 933 distal to valve 915 that extends away from body 920. Action pin 932 further includes an action end proximal to valve 915 that interacts with pin spring 934. Pin spring 934 is coupled between the action end of pin 932 and valve 915 and situated to resist lateral movement of action pin 932 toward valve 915.

Protrusion pin 940 includes a frustoconical shaped head 941 and a bar shaped shaft 942 with a rectangular cross-section that is connected to an end of head 941 with the largest diameter. Head 941 of protrusion pin 940 is housed within a pin tunnel 946 in body 920 with an end of head 941 with the smaller diameter in contact with the shaft of action pin 932. Protrusion spring 944 is also housed within pin tunnel 946 and contacts the end of protrusion pin 940 with the larger diameter and the end of the tunnel 946 that is distal to action pin 932. Shaft 942 of protrusion pin 940 runs through the middle of protrusion spring 944 and acts to force protrusion pin 940 toward action pin 932. Shaft opening 948 extends from pin tunnel 946 to the outer surface of body 920 and is sized to allow shaft 942 to exit body 920 but to retain protrusion head 941 and protrusion spring 944 within body 920.

Securing system 930 operates to move protrusion shaft 942 out of or into body 920. In a secured state, pin spring 934 pushes action pin 932 away from valve 915 so that pressing end 933 extends away from body 920. In this state, action pin 932 applies a force to protrusion pin 440 to force protrusion shaft 442 outside of body 920. When a depressing force, stronger than a force exerted by pin spring 934, pushes pressing end 933 toward body 920, action pin 932 shifts toward valve 915. As action pin 932 shifts toward valve 915, the diameter of action pin 932 in contact with protrusion head 941 decreases. As a result, protrusion spring 944 forces protrusion 940 further into body 920 and draws protrusion shaft 942 into body 920. In this position, securing system 930 is in an unsecured state. Once the depressing force is no longer applied to action pin 932, pin spring 934 shifts action pin 932 back to its original position. As action pin 932 shifts back, the diameter of the shaft of action pin 932 in contact with protrusion head 941 increases, thereby shifting protrusion pin 940 out of body 920 and pushing protrusion shaft 942 back out of body 920. The securing system 930 thereby returns to the securing state. The force required to cause securing system 930 to return to the unsecured state should not be more than could be applied by a surgeon.

In use, valve assembly 900 is coupled to handpiece 800. Securing system 930 is used to secure valve assembly 900 to handpiece 800. In particular, protrusion end 942 interacts with handpiece 800 to secure valve assembly 900 to handpiece 800. In the secured state, protrusion end 942 is extended and interacts with valve assembly 900. In the unsecured state, protrusion end 942 is retracted and valve assembly 900 may be installed on or removed from the handpiece 800.

When valve assembly 900 is secured to handpiece 800, valve 915 is used to control suction produced by handpiece 800 by connecting or disconnecting suction passageways in handpiece 800. For example, valve 915 may be rotated so that opening 917 is aligned with suction passageways of handpiece 800, thereby connecting the suction passageways together and allowing suction of material through handpiece 800. Valve 915 may also be rotated so that opening 917 is not aligned with the suction passageways of handpiece 800, thereby disconnecting the suction passageways and eliminating suction through handpiece 800.

Figure 3:
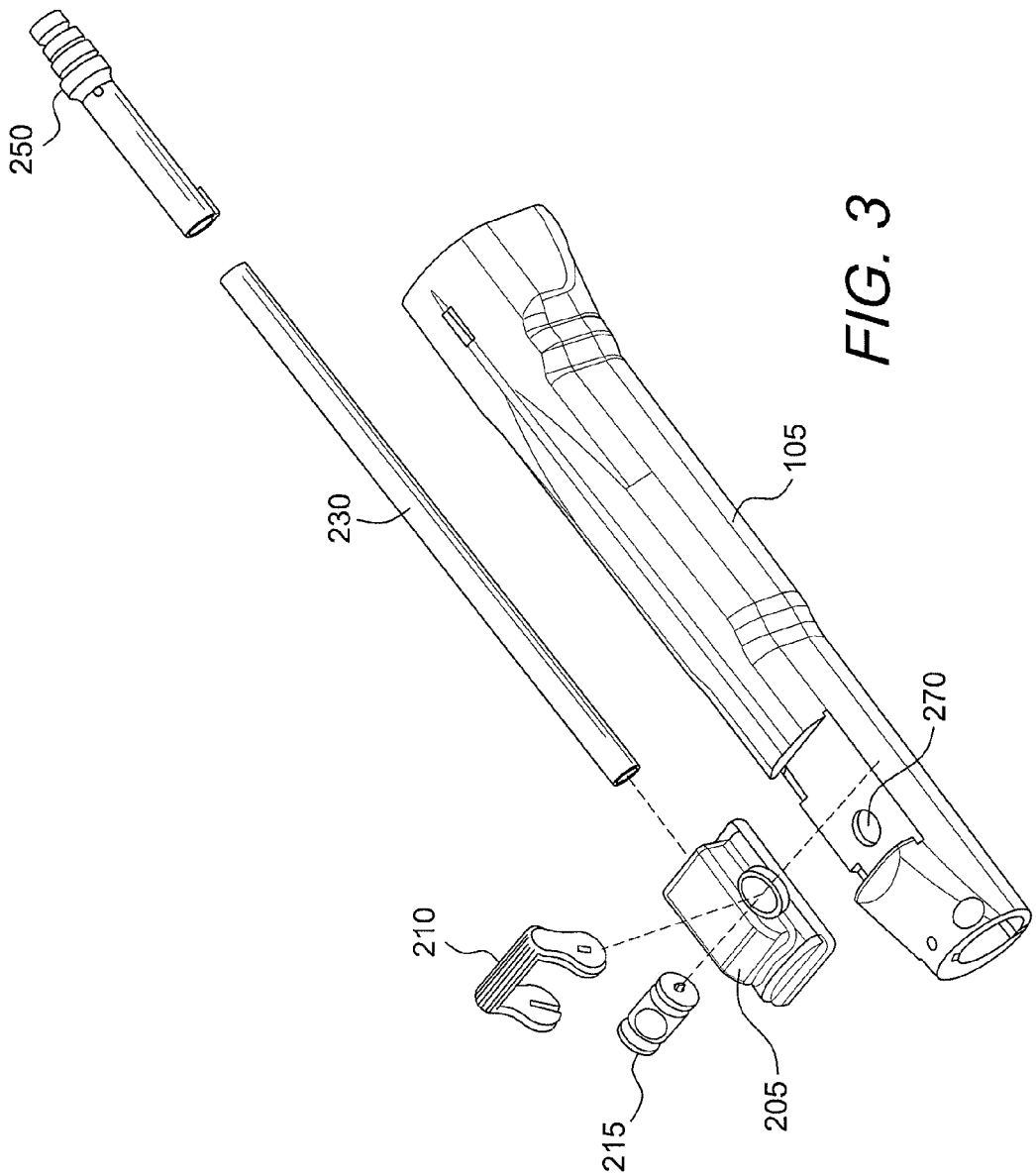
FIG. 3 is an exploded view of the powered handpiece of FIG. 1.
Figure 4:
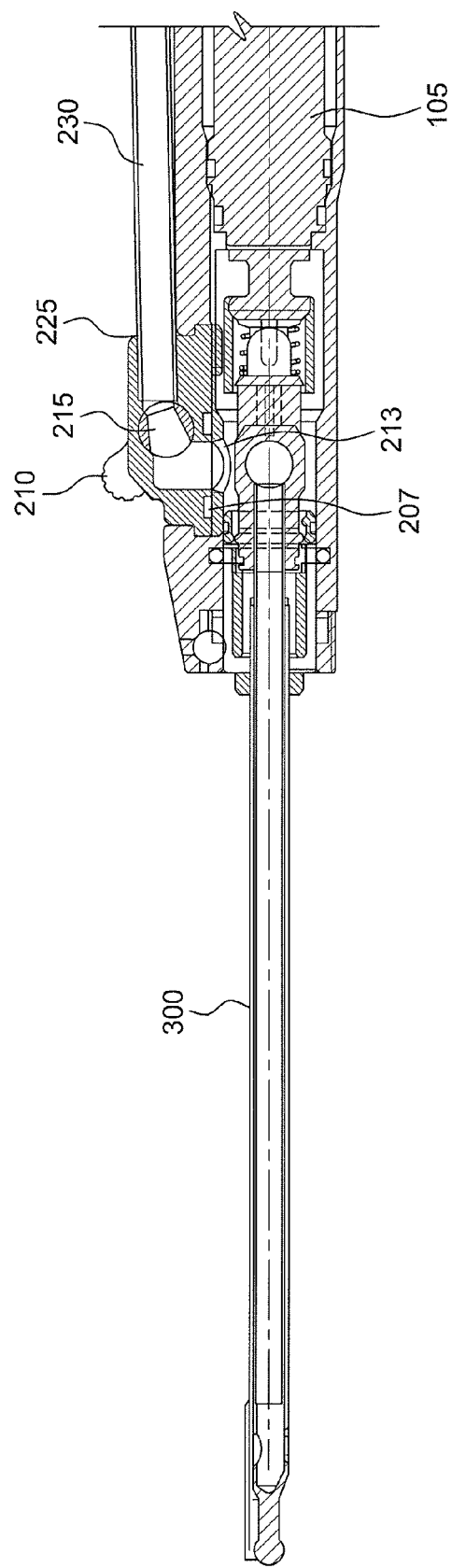
FIG. 4 is a sectional view of the powered handpiece/surgical instrument of FIG. 2, with the suction valve assembly in the open position.
Figure 5:
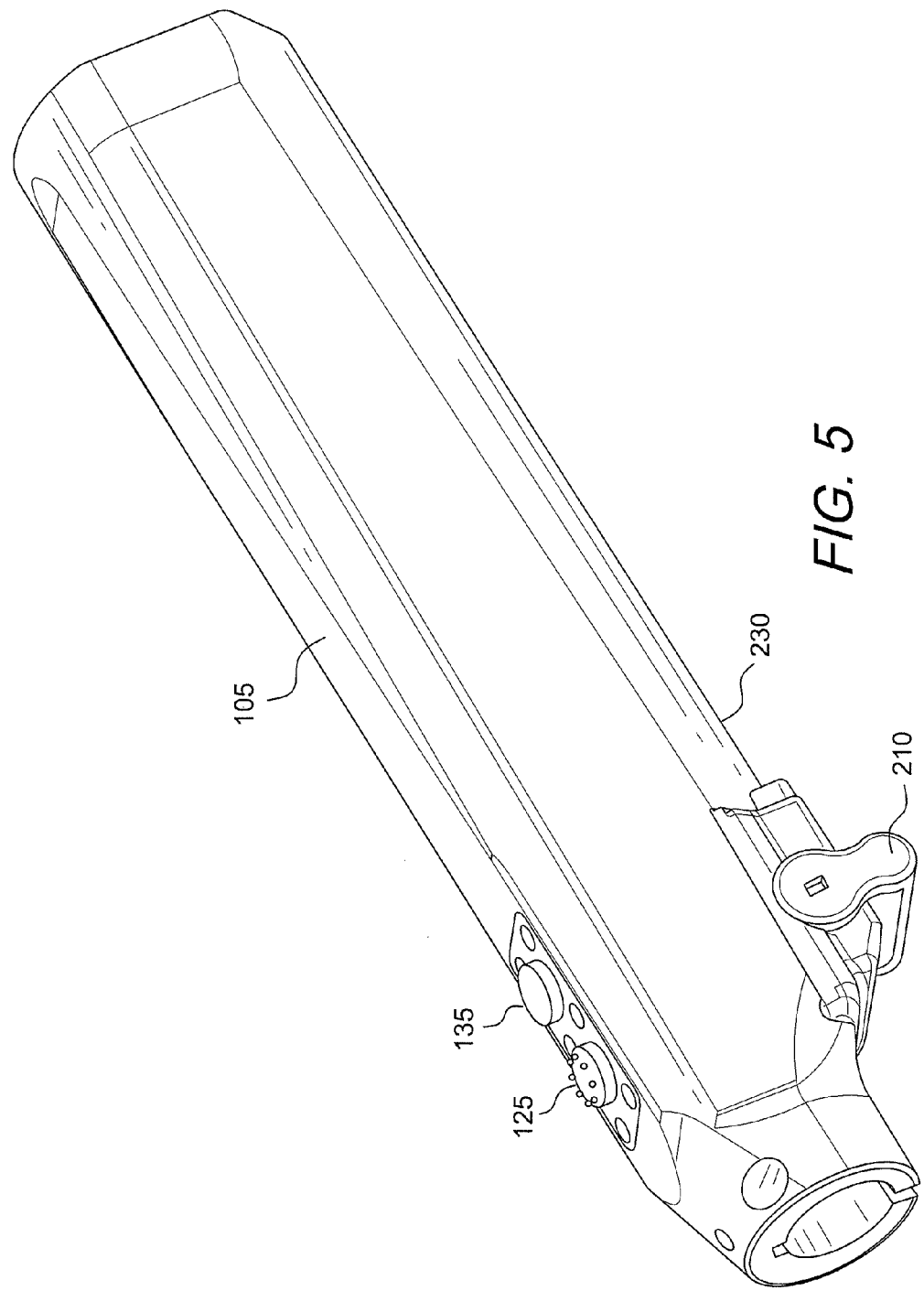
FIG. 5 illustrates a perspective view of another exemplary embodiment of a powered handpiece of the present invention, having pushbutton controls and an internal suction passageway.
Figure 6:
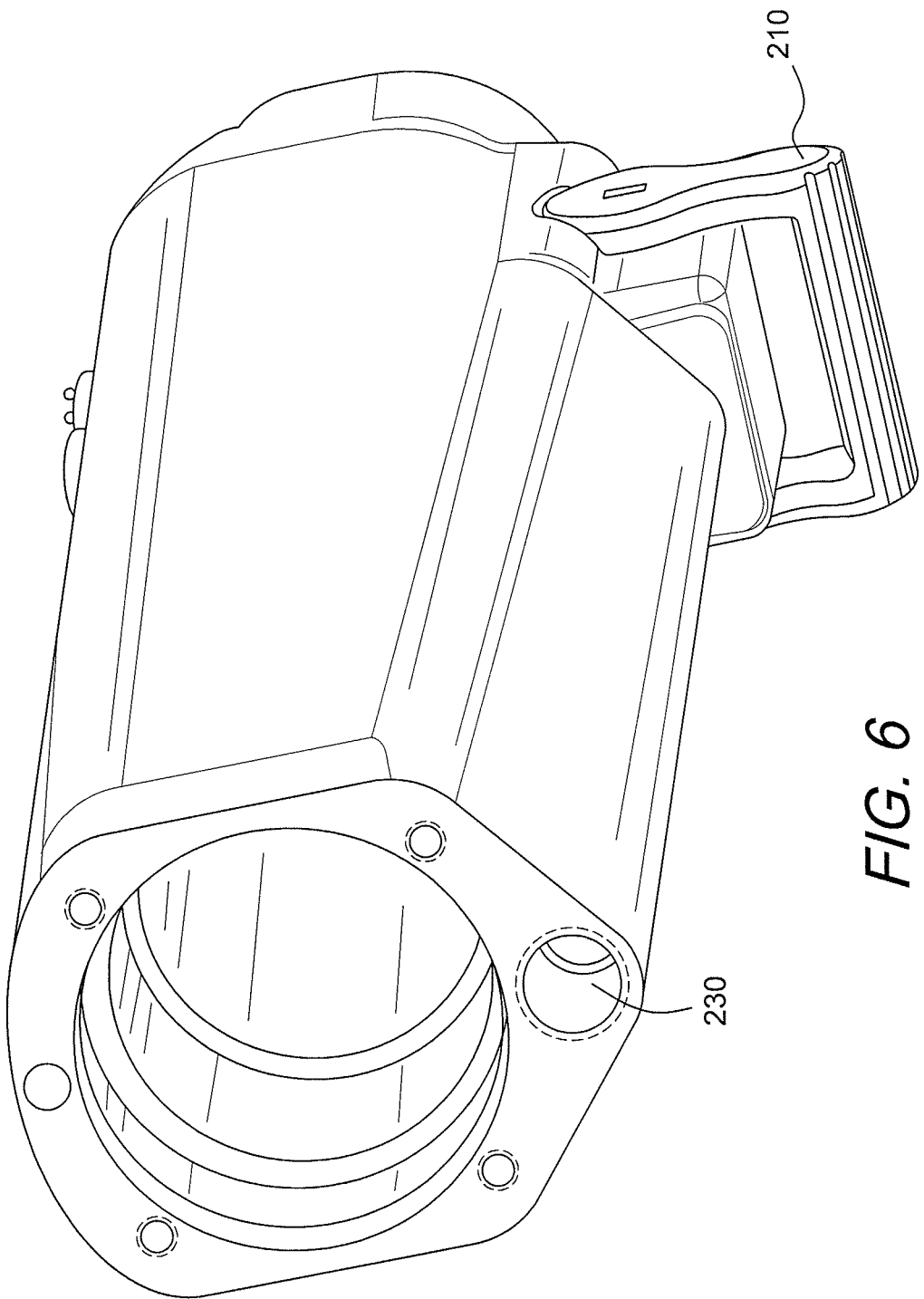
FIG. 6 illustrates a perspective view from the proximal end of the powered handpiece of FIG. 5.
Figure 7:
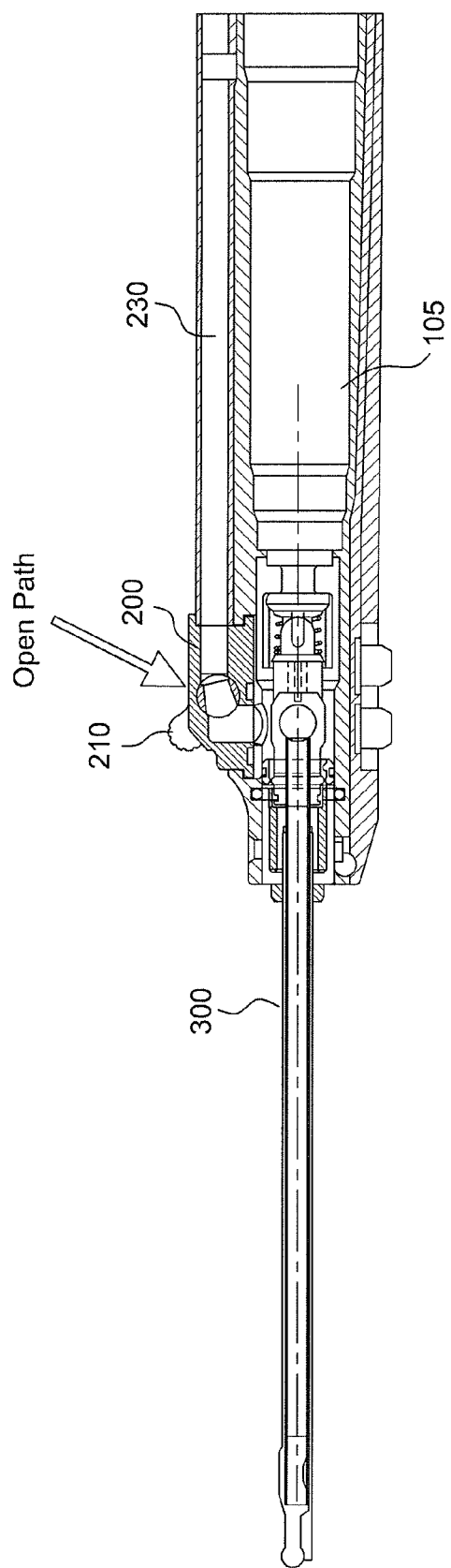
FIG. 7 illustrates a sectional view of the handpiece in FIG. 5 (with a surgical instrument attached to the powered handpiece), and with the valve assembly in an open position.
Figure 8:
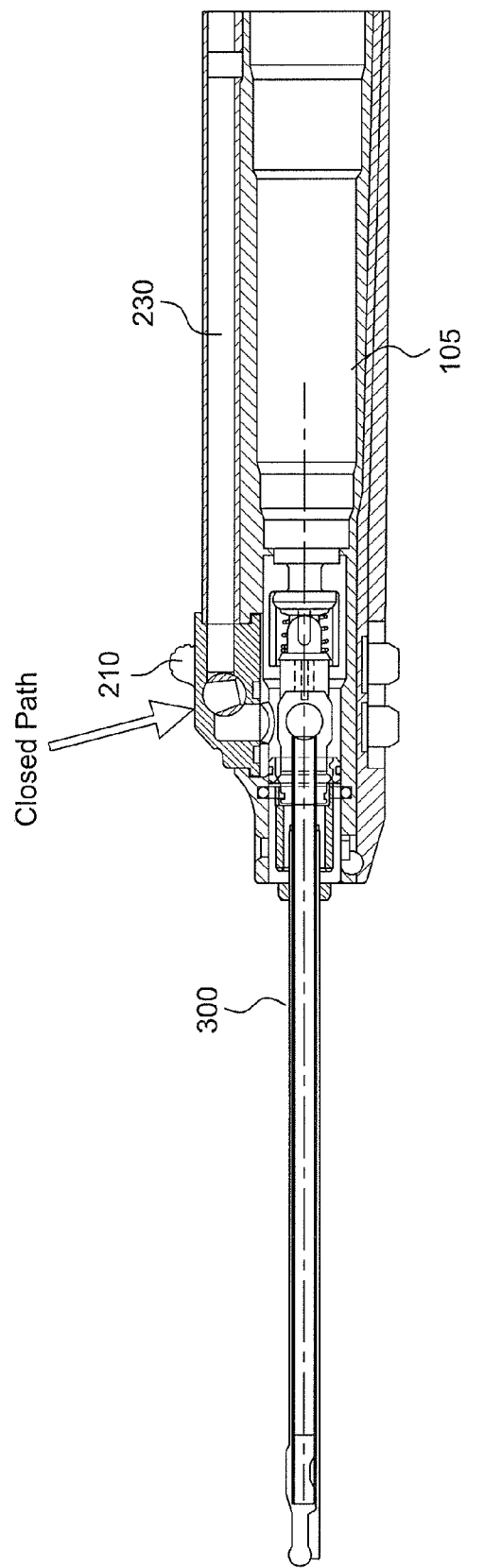
FIG. 8 illustrates a sectional view of the handpiece of FIG. 5 (with a surgical instrument attached to the powered handpiece), and with the suction valve assembly in a closed position.

In addition to the valve assembly being removable, the suction/aspiration passageway 230 could also be removable and disposable. As shown in FIGS. 1 and 3, the suction/aspiration passageway is external to the handpiece and may be removable for cleaning of the remaining portions of the suction/aspiration passageway. Preferably, the removable portion of the suction/aspiration passageway would be connected to the valve assembly such that both the valve assembly and the portion of the suction/aspiration passageway would be removable as one piece. The removable portion of the aspiration passageway may be manufactured from plastic or metal materials such as stainless steel, aluminum, PEEK, radel, ultem.

In some models of handpieces, the suction/aspiration passageway is an integral portion of the handpiece housing 105 as shown in FIGS. 5-8. The suction/aspiration passageway 230 is formed within the housing of the handpiece, extending from a proximal end to a distal end. The removable valve assembly 200 functions the same way to provide access to the suction/aspiration passageway for cleaning.

Figure 11:
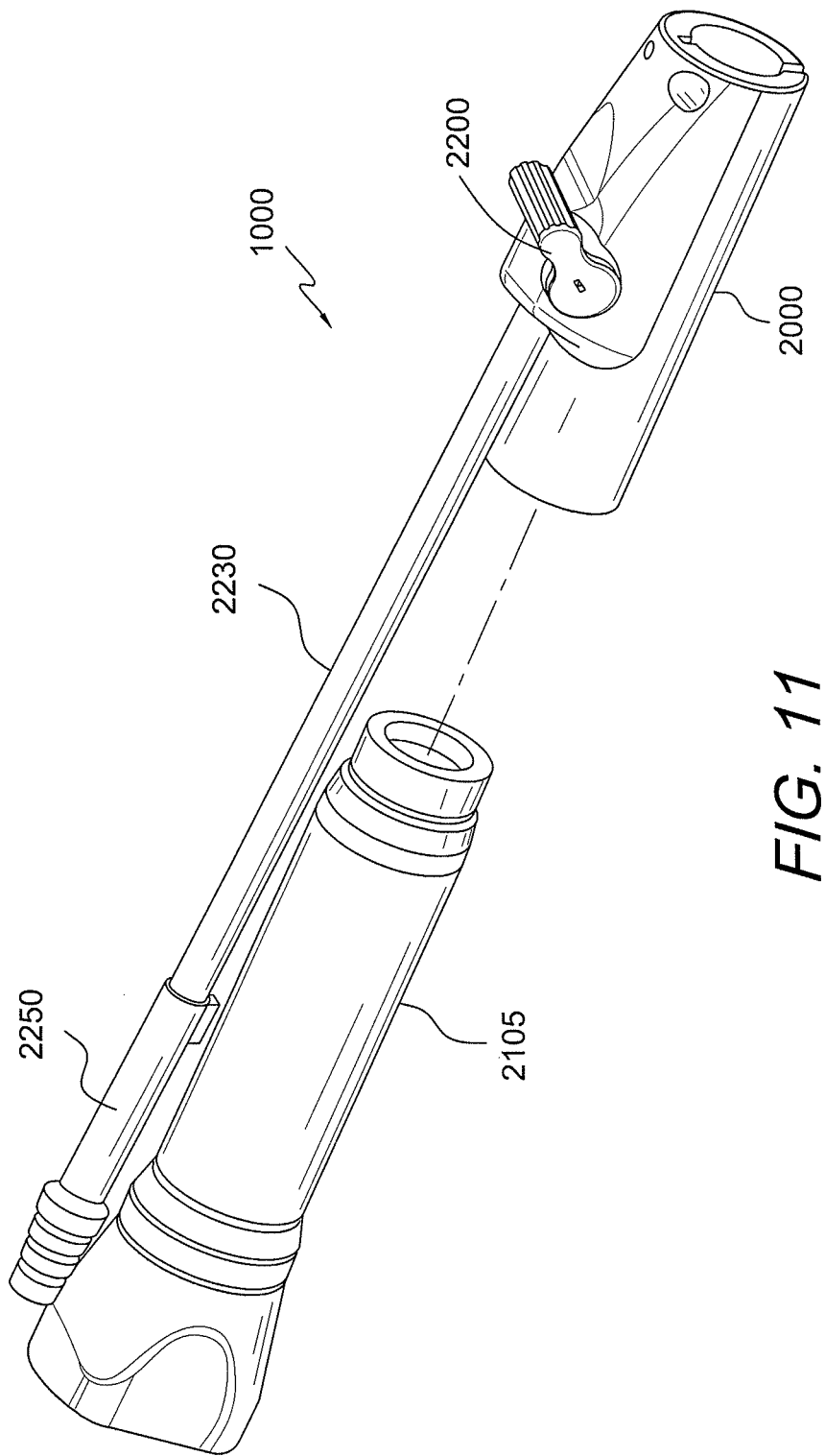
FIGS. 11 and 12 illustrate an alternate embodiment of a handpiece having a removable collet with a suction valve.
Figure 12:
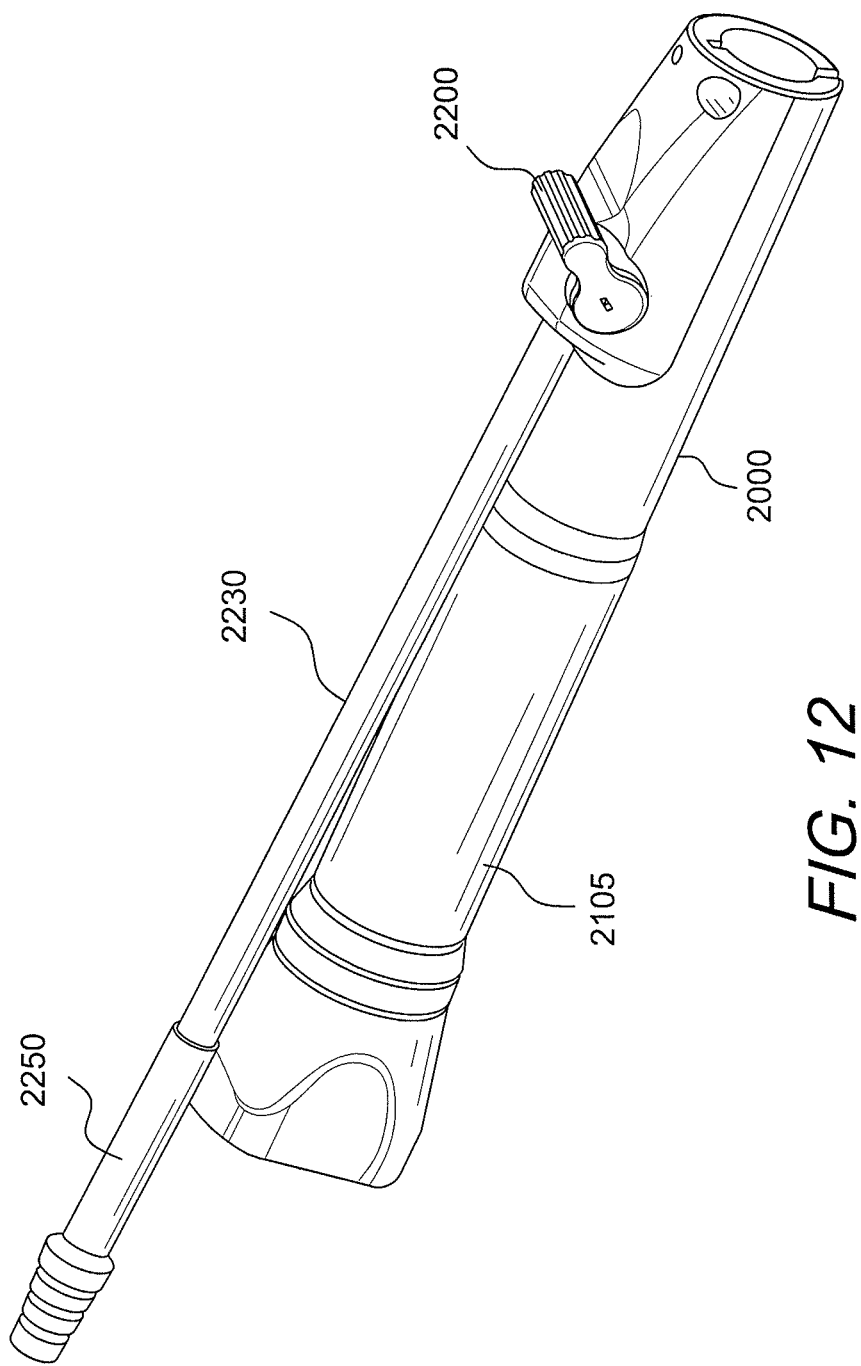

In an alternate embodiment, the entire distal end of the handpiece may be removable for cleaning. This embodiment would be more preferable in the foot control handpiece as the electrical communication portion resides in the foot control rather than the handpiece itself. As shown in FIGS. 11 and 12, surgical handpiece 1000 includes a removable collet assembly 2000 having a suction valve assembly 2200, a housing 2105, a suction/aspiration passageway 2230 and a barb connector 2250. The collet assembly 2000 may be removable in any number of ways known to one skilled in the art such as threading, snap fit, or quick connect coupling. The suction valve assembly 2200 connects the first suction/aspiration passageway 2230 to the second suction/aspiration passageway of the surgical instrument. The suction valve assembly 2200 works the same as suction valve 200 to open and close the suction/aspiration passageway. The removable collet 2000 may be disposed of after use to prevent any tissue debris from remaining within the handpiece and a new clean collect may be provided for additional use of the handpiece. The first suction/aspiration passageway may also be removable and disposable to prevent tissue debris from remaining during additional use of the handpiece.

The handpiece of the present invention may be used in many different surgical areas including, but not limited to, arthroscopy, laproscopy, maxillo-facial dental and cranial applications.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description, but rather only by the appended claims.

What is claimed as new and desired to be protected by Letters Patent of the United States is:

1. A surgical handpiece, comprising:
   a first suction passageway;
   a second suction passageway; and
   a removable valve assembly for connecting or disconnecting the first suction passageway to the second suction passageway, the valve assembly comprising a protrusion for engaging the handpiece to secure the valve assembly to the handpiece, the valve assembly further comprising a spring that applies a force to the protrusion to disengage the protrusion from the handpiece, an action pin coupled to the protrusion and an action pin spring that interacts with the action pin, wherein the action pin extends perpendicular to the protrusion and applies a force to the protrusion to overcome the force of the spring and engage the protrusion with the handpiece, and wherein the action pin spring opposes movement of the action pin in a first direction.

2. The surgical handpiece of claim 1, wherein the valve assembly and the first suction passageway are removable from the handpiece.

3. The surgical handpiece of claim 1, wherein the protrusion disengages the handpiece by retracting away from the handpiece.

4. The surgical handpiece of claim 3, wherein a portion of the protrusion enters the valve assembly when the protrusion retracts away from the handpiece.

5. The surgical handpiece of claim 1, wherein the action pin moves along an action pin movement axis that is perpendicular to an axis of movement of the protrusion.

6. The surgical handpiece of claim 1, wherein movement of the action pin spring in the first direction disengages the protrusion with the handpiece.

7. The surgical handpiece of claim 5, wherein a diameter of the action pin varies along the action pin movement axis.

8. The surgical handpiece of claim 1, wherein a part of the protrusion that engages with the handpiece has a rectangular cross-section.

9. The surgical handpiece of claim 1, wherein the valve assembly can rotate when secured to the handpiece.

10. The surgical handpiece of claim 9, wherein the valve assembly rotates between an open position connecting the first and second suction passageways and a closed position disconnecting the first and second suction passageways.

11. A surgical handpiece, comprising:
    a housing with a cavity;
    a first suction passageway extending away from the cavity;
    a second suction passageway extending away from the cavity; and
    a removable valve assembly for connecting or disconnecting the first suction passageway to the second suction passageway, the valve assembly comprising a protrusion, the protrusion engaging the handpiece to secure the valve assembly within the cavity, the valve assembly further comprising a spring that applies a force to the protrusion to disengage the protrusion from the handpiece, an action pin coupled to the protrusion and an action pin spring that interacts with the action pin, wherein the action pin extends perpendicular to the protrusion and applies a force to the protrusion to overcome the force of the spring and engage the protrusion with the handpiece, and wherein the action pin spring opposes movement of the action pin in a first direction.

12. The surgical handpiece of claim 11, wherein the protrusion disengages the handpiece by retracting away from the handpiece.

13. The surgical handpiece of claim 12, wherein the valve assembly can rotate when secured to the handpiece.

14. The surgical handpiece of claim 13, wherein the valve assembly further comprises a body, the body having an opening that extends through the body.

15. The surgical handpiece of claim 14, wherein in an open position the opening of the valve assembly aligns with and connects the first and second suction passageways and in a closed position the opening of the valve assembly is not aligned with and disconnects the first and second suction passageways.

16. A method for cleaning a surgical handpiece comprising:

providing a removable valve assembly for connecting or disconnecting a first suction passageway to a second suction passageway, the valve assembly comprising a protrusion that engages the handpiece to secure the valve assembly to the handpiece, wherein a spring applies a force to the protrusion to disengage the protrusion from the handpiece, and wherein the valve assembly further comprises an action pin coupled to the protrusion and an action pin spring that interacts with the action pin, wherein the action pin extends perpendicular to the protrusion and applies a force to the protrusion to overcome the force of the spring and engage the protrusion with the handpiece, and wherein the action pin spring opposes movement of the action pin in a first direction;

removing the valve assembly by retracting the protrusion; and cleaning a portion of at least the first and second suction passageways that was previously inaccessible.

17. The method of claim 16, further comprising replacing the valve assembly, wherein the valve assembly reengages the handpiece.

18. The method of claim 16, wherein the step of removing the valve assembly further comprises pressing the action pin coupled to the protrusion to retract the protrusion so that the protrusion disengages the handpiece.

19. The method of claim 18, wherein the action pin is part of the valve assembly.

20. The method of claim 16, wherein a portion of the protrusion enters the valve assembly when the protrusion is retracted.

21. The method of claim 16, further comprising disposing of the removable valve assembly.

* * * * *